United States Patent
Nassutt et al.

(10) Patent No.: US 12,096,947 B2
(45) Date of Patent: Sep. 24, 2024

(54) BONE MARROW HARVESTING DEVICE AND STORAGE METHODS

(71) Applicant: Stryker European Operations Holdings LLC, Kalamazoo, MI (US)

(72) Inventors: Roman Nassutt, Kiel (DE); Robin Büscher, Heikendorf (DE); Nils Reimers, Kiel (DE)

(73) Assignee: Stryker European Operations Holdings LLC, Portage, MI (US)

( * ) Notice: Subject to any disclaimer, the term of this patent is extended or adjusted under 35 U.S.C. 154(b) by 302 days.

(21) Appl. No.: 17/668,710

(22) Filed: Feb. 10, 2022

(65) Prior Publication Data

US 2022/0160374 A1 May 26, 2022

Related U.S. Application Data

(60) Continuation of application No. 16/293,745, filed on Mar. 6, 2019, now Pat. No. 11,259,819, which is a
(Continued)

(51) Int. Cl.
*A61B 17/16* (2006.01)
*A61B 10/02* (2006.01)
(Continued)

(52) U.S. Cl.
CPC ........ *A61B 17/1635* (2013.01); *A61B 10/025* (2013.01); *A61B 17/164* (2013.01);
(Continued)

(58) Field of Classification Search
CPC .............. A61B 17/1635; A61B 17/164; A61B 17/1659; A61B 10/025; A61B 2017/00473
See application file for complete search history.

(56) References Cited

U.S. PATENT DOCUMENTS 5,694,951 A 12/1997 Bonutti
5,993,387 A 11/1999 Moore et al.
(Continued)

FOREIGN PATENT DOCUMENTS

CN 1432645 A 7/2003

OTHER PUBLICATIONS

G. Cox et al., The use of the reamer-irrigator-aspirator to harvest mesenchymal stem cells, J Bone Joint Surg [Br];93-B:517-24, 2011.
(Continued)

*Primary Examiner* — Sameh R Boles
(74) *Attorney, Agent, or Firm* — Lerner David LLP

(57) ABSTRACT

Bone harvesting tools and methods of use thereof are disclosed. In an embodiment, the tool comprises a chamber having a first aperture, a second aperture, an internal cavity, and a suction source fluidly connected with the chamber. The suction source is effective to generate negative pressure within the internal cavity of the chamber. The tool also has a reamer having a reaming portion, the reamer being sized to extend through the first and second apertures of the chamber, wherein the reamer is movable relative to the chamber. Additionally, the tool includes a storage container fluidly connected to the internal cavity of the chamber and effective to receive bone and/or cellular material extracted from the patient, the bone and/or cellular material being extracted during reaming a bone of the patient with the reamer.

20 Claims, 5 Drawing Sheets

Related U.S. Application Data division of application No. 15/078,630, filed on Mar. 23, 2016, now Pat. No. 10,231,743.

(60) Provisional application No. 62/137,521, filed on Mar. 24, 2015.

(51) Int. Cl.
 *A61B 17/00* (2006.01)
 *A61B 17/32* (2006.01)

(52) U.S. Cl.
 CPC .. *A61B 17/1659* (2013.01); *A61B 2010/0258* (2013.01); *A61B 2017/00473* (2013.01); *A61B 2017/00969* (2013.01); *A61B 2017/320064* (2013.01); *A61B 2217/005* (2013.01)

(56) References Cited

U.S. PATENT DOCUMENTS

| | | | |
|---|---|---|---|
| 6,022,354 | A | 2/2000 | Mercuri et al. |
| 6,071,284 | A * | 6/2000 | Fox ................... A61B 17/1635 606/80 |
| 6,139,509 | A | 10/2000 | Yuan et al. |
| 6,325,806 | B1 | 12/2001 | Fox |
| 6,332,886 | B1 | 12/2001 | Green et al. |
| 6,387,070 | B1 | 5/2002 | Marino et al. |
| 6,440,138 | B1 | 8/2002 | Reiley et al. |
| 6,783,533 | B2 | 8/2004 | Green et al. |
| 8,038,679 | B2 | 10/2011 | Wieland |
| 8,425,518 | B2 | 4/2013 | Wieland |
| 2002/0099401 | A1 | 7/2002 | Bonutti |
| 2005/0010437 | A1 | 1/2005 | Abukwedar |
| 2008/0177200 | A1 | 7/2008 | Ikehara et al. |
| 2008/0189045 | A1 | 8/2008 | Moore |
| 2008/0195105 | A1 * | 8/2008 | Sidebotham ....... A61B 17/1617 606/80 |
| 2008/0215364 | A1 | 9/2008 | Brevnova et al. |
| 2009/0053282 | A1 | 2/2009 | Smiler et al. |
| 2009/0138354 | A1 | 5/2009 | Zech |
| 2010/0298835 | A1 | 11/2010 | Ralph et al. |
| 2011/0054929 | A1 | 3/2011 | Centeno |
| 2011/0262405 | A1 | 10/2011 | Segina et al. |
| 2012/0052049 | A1 | 3/2012 | Woods et al. |
| 2013/0052169 | A1 | 2/2013 | Marom |
| 2013/0253519 | A1 | 9/2013 | Mitchell et al. |
| 2015/0193581 | A1 | 7/2015 | Kaminski et al. |
| 2015/0216539 | A1 | 8/2015 | Reimers et al. |

OTHER PUBLICATIONS

Sterigraft, Bone Bank Allografts, website printout, Jan. 23, 2014.
International Search Report and Written Opinion for Application No. PCT/US2015/014814 dated Apr. 9, 2015.
Perry et al., "Collection, Cryopreservation, and Characterization of Human Dental Pulp-Derived Mesenchymal Stem Cells for Banking and Clinical Use", Tissue Engineering: Part C, vol. 14, No. 2, 2008.
Nielsen, et al., "Bone Bank Service in Odense, Denmark. Audit of the First Ten Years with Bone Banking at the Department of Orthopaedics, Odense University Hospital", vol. 2, No. 3, Cell and Tissue Banking, Sep. 2001, pp. 179-183.
Extended European Search Report and Written Opinion for EP Application No. 15705463.6, dated Aug. 28, 2018.
Porter et al. "Osteogenic Potential of Reamer Irrigator Aspirator (RIA) Aspirate Collected from Patients Undergoing Hip Arthroplasty". J Orthop Res. Jan. 2009; 27(1): 42-49. 2009.

* cited by examiner

BONE MARROW HARVESTING DEVICE AND STORAGE METHODS

CROSS-REFERENCE TO RELATED APPLICATIONS

This application is a continuation of U.S. patent application Ser. No. 16/293,745, filed on Mar. 6, 2019, which is a divisional of U.S. patent application Ser. No. 15/078,630, filed on Mar. 23, 2016, now U.S. Pat. No. 10,231,743, and claims the benefit of the filing date of U.S. Provisional Patent Application No. 62/137,521, filed on Mar. 24, 2015, the disclosures of which are each hereby incorporated in their entireties herein by reference.

BACKGROUND OF THE INVENTION

The present invention relates to devices and methods of harvesting bone and/or cellular material for use in various medical treatments.

The Applicant has devised novel and useful methods for harvesting bone and/or cellular material in a single-stage procedure, as described in co-pending U.S. patent application Ser. No. 14/616,071, titled "Bone Marrow Harvesting and Storage" ("the '071 Application"), the disclosure of which is incorporated by reference herein. Particular devices useful for extracting bone and/or cellular material, in the manner set forth in the '071 Application or otherwise, would be useful, however. The present invention(s) provides such a device, as well as further extraction methods.

BRIEF SUMMARY OF THE INVENTION

A first aspect of the invention includes a bone harvesting tool for extraction of bone and/or cellular material from a patient during a surgical procedure. The tool comprises a chamber having a first aperture, a second aperture, an internal cavity, and a suction source fluidly connected with the chamber, the suction source being effective to generate negative pressure within the internal cavity of the chamber. A reamer having a reaming portion is also included with the tool, the reamer being sized to extend through the first and second apertures of the chamber, wherein the reamer is movable relative to the chamber. Last, the tool has a storage container fluidly connected to the internal cavity of the chamber and effective to receive bone and/or cellular material extracted from the patient, the bone and/or cellular material being extracted during reaming a bone of the patient with the reamer.

In an embodiment of the first aspect, the chamber includes a first seal effective to contact skin and/or tissue of the patient, and a second seal spaced apart from the first seal. Optionally, the storage container may be a handle of the bone harvesting tool that is removable from the bone harvesting tool. The bone harvesting tool is usable in surgical procedures to obtain and collect bone marrow, cortical and cancellous bone (e.g., bone chips), and other bone material for a variety of different medical uses. The tool and its components are optionally packaged in a sterile package prior to use (e.g., a single-use sterile package) so that the tool is easily usable in a surgical procedure involving the drilling of bone.

A second aspect of the invention includes a method of collecting bone and/or cellular material during a surgical procedure. The method comprises: (a) positioning a bone harvesting tool having a first seal and a second seal against a patient's skin and/or tissue so that the first seal establishes a fluid-tight seal at the location of the patient's skin and/or tissue; (b) operating a reamer extending through the first and second seals so that a reaming portion of the reamer drills into a bone of the patient and creates bone and/or cellular material; (c) generating negative pressure within an internal cavity of the bone harvesting tool, the negative pressure causing the bone and/or cellular to flow from the patient and into the internal cavity; and (d) collecting the bone and/or cellular material in a storage container removably and fluidly connected to the internal cavity of the bone harvesting tool.

Although the steps above are lettered in the second aspect, no particular order of the steps is intended or implied by the lettering. In an embodiment of the second aspect, the method also comprises identifying a set of patients undergoing an existing surgical operation in which bone and/or cellular material is to be removed from the patient, screening the set of patients using certain criteria to ascertain a subset of patients who qualify to donate bone and/or cellular material, wherein a first aspect of the criteria requires the subset of patients to be undergoing an existing operation in the ordinary course of events, which is not a surgery dedicated predominantly to extracting the bone and/or cellular material, and selecting the patient from the subset of patients and performing steps (a) through (d). The surgical operation may be an orthopedic operation involving reaming of a bone of the patient, in particular a medullary canal of the bone.

A third aspect of the invention includes a method of collecting bone and/or cellular material during a surgical procedure. The method comprises: (a) positioning a bone harvesting tool having a seal against a patient's skin and/or tissue so that the seal establishes a fluid-tight seal at the location of the patient's skin and/or tissue; (b) operating a reamer extending through the seal so that a reaming portion of the reamer drills into a bone of the patient and creates bone and/or cellular material; and (c) generating negative pressure within the bone harvesting tool, the negative pressure causing the bone and/or cellular to flow from the patient and into a storage container removably and fluidly connected to the seal of the bone harvesting tool.

Although the steps above are lettered in the third aspect, no particular order of the steps is intended or implied by the lettering.

BRIEF DESCRIPTION OF THE DRAWINGS

A more complete appreciation of the subject matter of the present invention and of the various advantages thereof can be realized by reference to the following detailed description in which reference is made to the accompanying drawings in which.

DETAILED DESCRIPTION

In describing particular embodiments of the present invention, specific terminology will be used for the sake of clarity. However, the invention is not intended to be limited to any specific terms used herein, and it is to be understood that each specific term includes all technical equivalents, which operate in a similar manner to accomplish a similar purpose.

As used herein, the phrase bone and/or cellular material refers to material that is extractable from bone, which optionally may be processed and/or separated to produce another material. For instance, bone and/or cellular material may include cancellous bone, cortical bone (in the form of chips or morselized bone), bone marrow material, or stem cells produced from any of the foregoing materials. Such materials frequently are found, for example, in the medullary canal (as well as the bone surrounding the canal) of a long bone.

Figure 1:
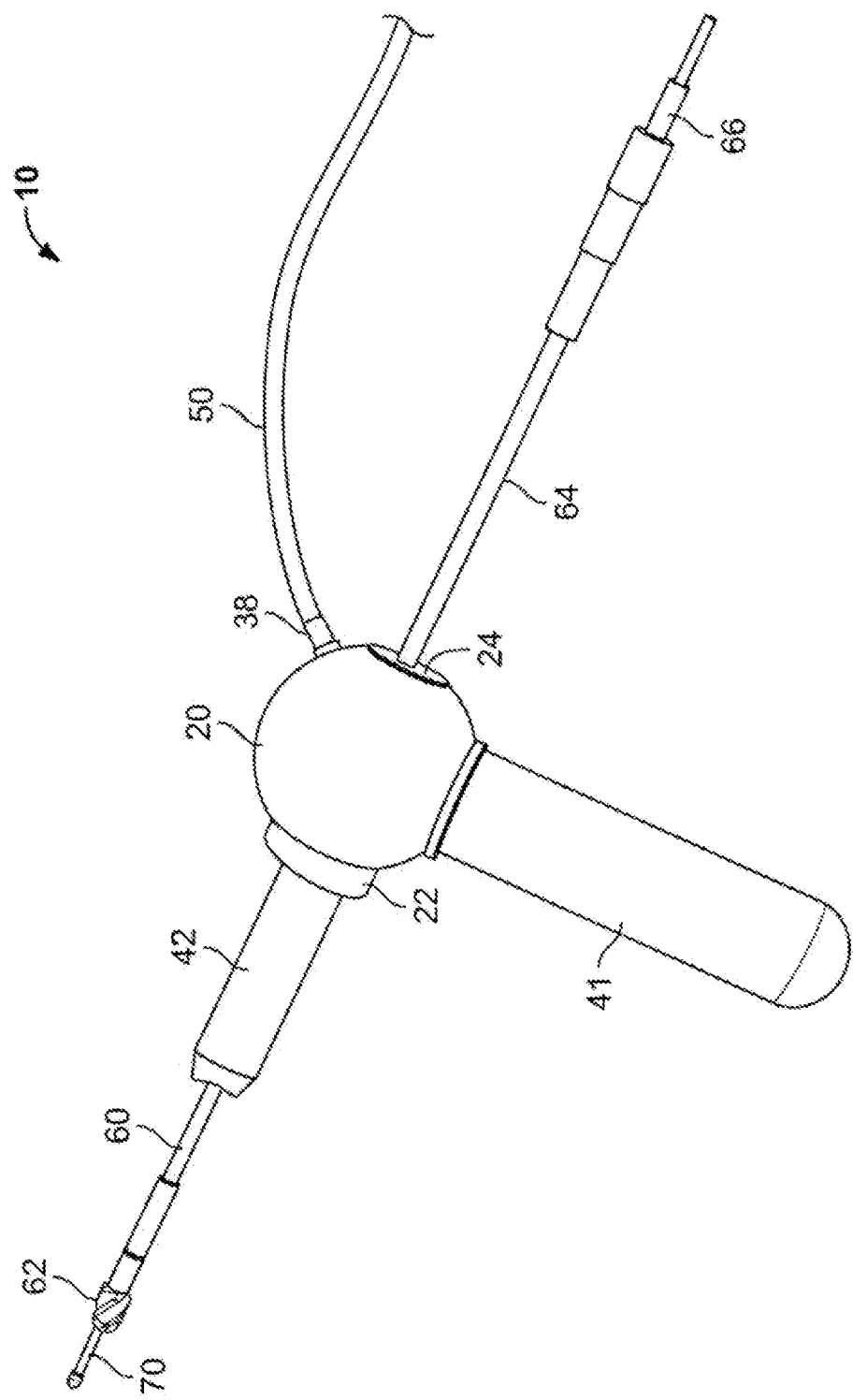
FIG. 1 is a perspective view of a bone harvesting instrument according to an embodiment of the present invention.

Referring to FIG. 1, a bone harvesting instrument 10 is shown. Instrument 10 includes a chamber 20, in one embodiment shaped as a ball or sphere, and a reaming or drilling implement 60 extending through chamber 20. A sleeve 42 extends outwards from chamber 20, and a suction tube 50 is connected thereto for providing negative pressure and suction in the vicinity of chamber 20. A storage container 41 is also fluidly connected with chamber 20. In this way, bone harvesting instrument 10 can be used to ream or drill bone using reamer 60, and extract bone and/or cellular material therefrom through sleeve 42 and into storage handle 41 for immediate or later use. Such bone and/or cellular material is typically in the form of bone marrow material in the intramedullary canal of the bone being reamed, as well as surrounding cancellous and cortical bone.

Figure 2:
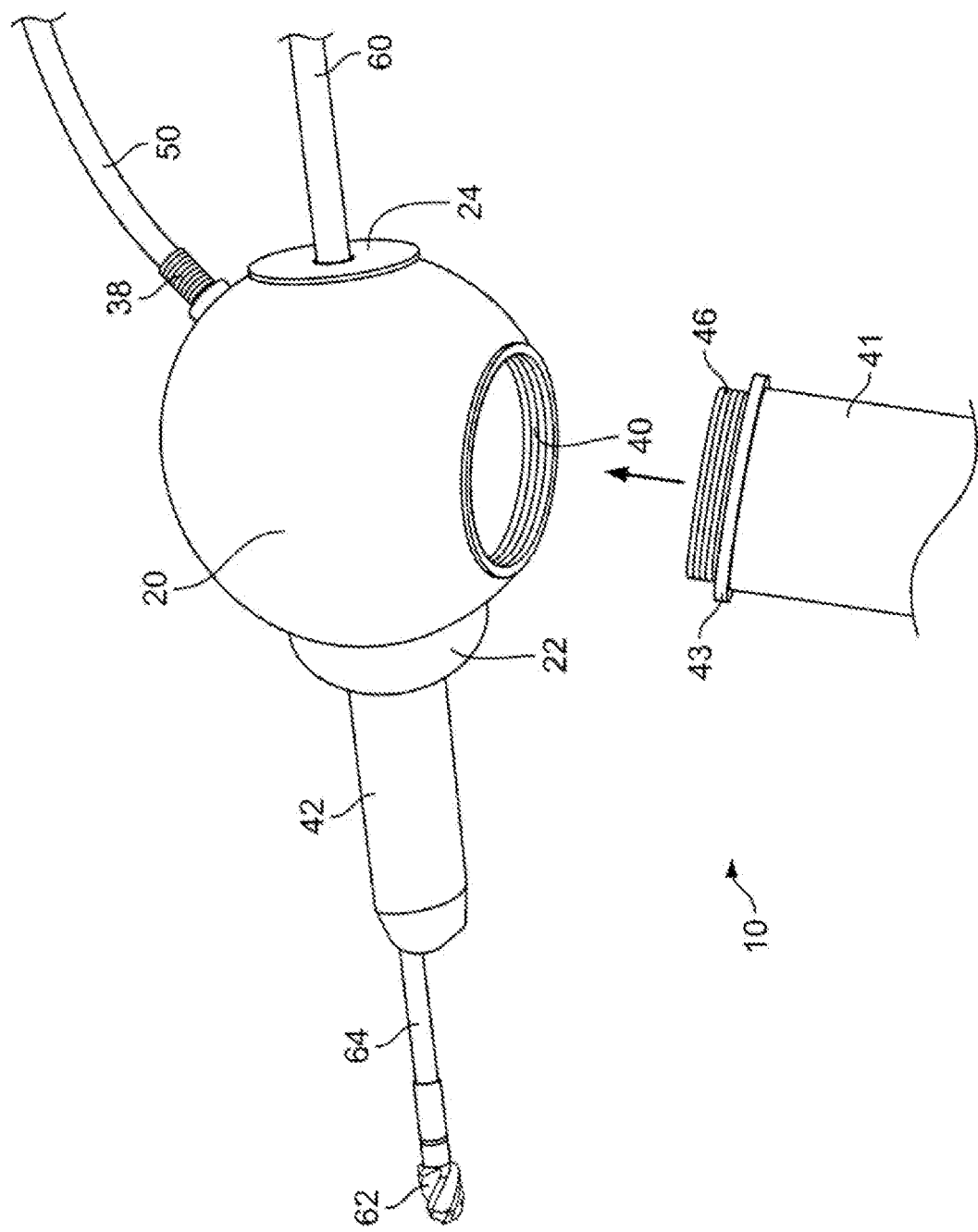
FIG. 2 is a close-up exploded perspective view of several components of the bone harvesting instrument of FIG. 1.
Figure 3:
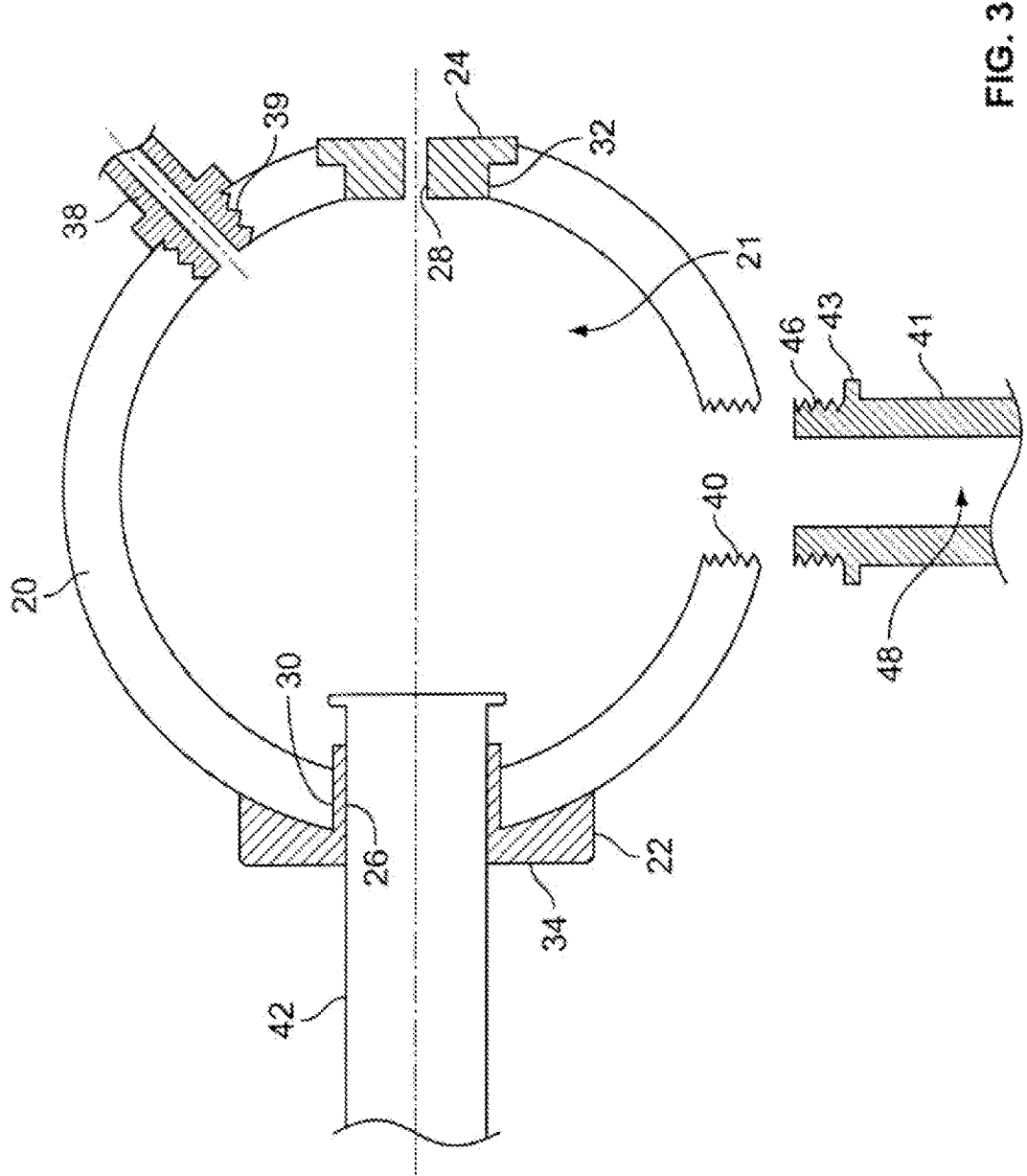
FIG. 3 is a cross-sectional view of several components of the bone harvesting instrument of FIG. 1.

As shown in FIGS. 1 and 3, chamber 20 is, in an embodiment, spherical in shape and includes a hollow internal cavity 21. Apertures 30, 32 extend through chamber 20 and are sized to accommodate respective first and second sealing members 22, 24. Sealing members 22, 24 may be roughly cylindrical in shape with substantially flat ends. As an example, first seal 22 may be arranged to contact skin and/or tissue of a patient during a surgical procedure to establish a fluid-tight seal therewith, and thus, it may have a substantially flat skin/tissue facing surface 34, as shown in FIG. 3. In an embodiment, surface 34 is angled or tapered, such that the body of first seal 22 has a variable thickness. First and second seals 22, 24 also include openings 26, 28 sized to accommodate sleeve 42 and reamer 60, respectively, as shown in FIGS. 1-3. In a particular embodiment, openings 26, 28 each has a center that lies along a common axis, as shown in FIG. 3. Stated alternatively, openings 26, 28 are cylindrical in an embodiment and, if opening 28 were superimposed within opening 26, it would form a concentric cylinder within opening 26. This allows reamer 60 to be inserted into opening 28 and subsequently through sleeve 42 and opening 26 of first seal 22. Referring to FIG. 3, seals 22, 24 extend entirely through apertures 30, 32 to effectively establish a fluid-sealed environment within chamber 20 and thereby allow bone and/or cellular material to be drawn through chamber 20. First and second seals 22, 24 may be affixed to apertures 30, 32 through any suitable means, for example via adhesives, through mating geometries, other bonding techniques, or a combination of the foregoing. First and second seals 22, 24 may also be composed of any suitable sealing material, such as rubber, silicone, or a polymer or polymer composite.

Referring to FIGS. 2-3, chamber 20 also includes a set of threaded openings 39, 40. Threaded opening 39 is sized and configured to accept a connector 38 that, in one embodiment, includes a fluid channel therethrough. Connector 38 engages with opening 39 in a manner allowing suction tubing 50 to connect therewith and establish a fluid channel to a suction source (not shown). The suction source (not shown) may be either powered or manual and is effective to create negative pressure in tubing 50 and, consequently, within internal cavity 21 of chamber 20 for withdrawing bone and/or cellular material out of the patient. Threaded opening 40 is sized and configured to accept a threaded end 46 of storage handle 41, as shown in FIGS. 2-3.

Storage handle 41 includes a hollow cavity 48 for accepting extracted bone and/or cellular material, and a flange 43 for abutting against chamber 20 once storage handle 41 is engaged with chamber 20. By way of threaded end 46 and threaded opening 40, storage handle 41 can be easily disengaged from chamber 20 after the surgical procedure is complete and all bone and/or cellular material is within handle 41. Of course, other connection mechanisms are contemplated between handle 41 and chamber 20, such as a press-fit connection, bayoneted connection, or any other suitable locking or engagement mechanism.

As shown in FIGS. 1-2, instrument 10 may also include a drill or reamer 60. Reamer 60 has a shaft 64 that is sized to extend through opening 28 in second seal 24, into internal cavity 21 of chamber 20, and into and through sleeve 42 and first seal 22 housing sleeve 42. A distal end or portion of reamer 60 includes a reaming or drilling portion 62 that is optionally fluted. Further, shaft 64 of reamer 60 may be cannulated to allow a guide wire 70 (e.g., a K-wire) to be positioned therein. Shaft 64 is also flexible, in an embodiment, to permit directional movement of reamer 60 and its reaming end 62 during drilling. Reamer 60 additionally includes a proximal end or portion with a connection 66 for engaging with a powered or manual instrument (not shown) for rotating reamer 60 and drilling bone. In an embodiment, connection 66 may be keyed for insertion into a likewise keyed portion of the powered or manual instrument (not shown). As reflected in FIG. 3, shaft 64 of reamer 60 may be roughly the same size (e.g., in terms of diameter) as opening 28 in second seal 24 to establish a fluid-tight seal at that location, but shaft 64 may be substantially smaller in size (e.g., in terms of diameter) than sleeve 42 to allow bone and/or cellular material to pass over shaft 64, into sleeve 42, and subsequently through internal cavity 21 of chamber 20 and into handle 41.

In use, instrument 10 may extract bone and/or cellular material from a patient undergoing a surgical operation, for instance an already-scheduled surgical operation in the normal course of events. In this regard, instrument 10 may be used to practice any of the methods disclosed in Applicant's '071 Application, and thus, it may be used to collect bone and/or cellular material in a surgical procedure where standard operating procedure is to discard such material. Of course, instrument 10 may also be used in other surgical procedures, including procedures dedicated solely to the extraction of bone and/or cellular material.

Using the methods of the '071 Application as an example, instrument 10 may be used in an intramedullary (IM) nail procedure being conducted on a patient. During such a procedure, the bone and/or cellular material generated is normally discarded. However, using instrument 10, such bone and/or cellular material can be stored for further processing and use at a later time, for example as set forth in the '071 Application. In an embodiment, the surgeon may conduct the procedure by first making an appropriate incision(s) through the patent's skin and issue to access the surgical site (e.g., an intramedullary canal of a long bone), and then insert a K-wire 70 into the patient's bone to provide a path for reaching the surgical site. The surgeon may then position instrument 10 against the patient's skin. In particular, with the components of instrument 10 assembled, as shown in FIG. 1 (e.g., handle 41 connected to chamber 20, tube 50 engaged with connector 38, seals 22, 24 and sleeve 42 in place, and reamer 60 extending through chamber 20), reamer 60 may be positioned over K-wire 70 and moved towards the patient's bone for reaming. K-wire 70 may guide reamer 60 and sleeve 42 through the patient's skin and tissue until sleeve 42 extends therethrough and reamer 60 is adjacent the bone to be reamed. In this way, sleeve 42 may establish a channel leading into internal cavity 21 of chamber 20 for extraction of bone and/or cellular material.

Skin/tissue facing surface 34 of first seal 22 may also be placed against the patient's skin/tissue to establish a fluid-tight seal at that location. Such a fluid-tight seal effectively allows instrument 10 to maintain negative pressure within chamber 20 and not loose pressure at the location of the patient's skin/tissue. In an embodiment, first seal 22 may sit atop the patient's skin around the incision site, or it may be embedded somewhat below the patient's skin in tissue. In a modification, first seal 22 may be placed within the patient's tissue and against the bone being reamed to establish an effective seal. In any of the above cases, a fluid-tight seal is created via first seal 22 at the relevant location for creating a closed environment in instrument 10.

With instrument 10 in position, reaming of the patient's bone may take place using reamer 60, in particular its reaming end/portion 62. The surgeon may direct reaming end/portion 62 within the intramedullary canal of a patient's long bone (or the intramedullary canal of another bone) and, during the reaming process, bone and/or cellular material may be extracted. In particular, as the bone is reamed, negative pressure may be generated within internal cavity 21 of chamber 20 by way of connector 38, suction tube 50, and a manual or powered suction source (not shown). The negative pressure causes the bone and/or cellular material to exit the patient's intramedullary canal, travel into sleeve 42, into internal cavity 21 of chamber 20, and subsequently into storage handle 41. In this way, the extracted bone and/or cellular material never reaches the external environment and, rather, it is kept in a sterile environment and stored in storage handle 41. Indeed, in an embodiment, all of instrument 10's components may be packaged in a single-use sterile package so that such components are easily usable in the surgical procedure and the components do not adversely affect the quality or usability of the extracted bone and/or cellular material (e.g., since the components are pre-sterilized). As such, with the aforementioned procedure, the bone and/or cellular material is extracted from the patient and stored in storage handle 41, which may be of any suitable size, for later use or further processing. In an embodiment, a cap (not shown) is also provided with instrument 10 for sealing off and closing handle 41 once the bone and/or cellular material is collected therein.

As discussed in the '071 Application, the bone and/or cellular material extracted by instrument 10 can also be sent to a storage, separation, and processing facility (e.g., a "biobank") for use in a later surgical procedure involving the patient, or a different patient. The extracted bone and/or cellular material can be processed at the biobank and used in a multitude of different medical procedures, as set forth in more detail in the '071 Application. For example, the biobank may process the material to obtain stem cells for the patient's later use (or use by another, qualifying patient). It should be appreciated that any of the uses described in the '071 Application for bone and/or cellular material are applicable to the bone and/or cellular material discussed herein, including but not limited to use as stem cells, allograft material, autograft material, and other uses.

In a modification of the above, storage handle 41 may comprise separate individual containers for different uses of the bone and/or cellular material. As an example, storage handle 41 may comprise three (3) individual containers for bone and/or cellular material, a first container for typification of the donator (e.g., to determine blood type, etc.), a second container for safety/quality examination, and a third main container for cryogenic storage of the bone and/or cellular material (e.g., stem cells) for later use with that patient, or a different patient. In this way, instrument 10 can provide a convenient means of accumulating all the necessary materials needed for proper banking of the bone and/or cellular material for later use. In one embodiment, the three (3) separate containers are initially joined together, but can be detached and used for their separate purposes, as described above. In yet another embodiment, a valve(s) may be used to direct the extracted bone and/or cellular material into the desired three (3) individual containers, and a transparent level with volume markings may be included on storage handle 41 for determining the amount of material in each container. For example, the surgeon may use the valve(s) to direct bone and/or cellular material into the first container within storage handle 41 until the volume thereof is at an acceptable level (e.g., as determined by the transparent level with volume markings), and then the valve(s) could be actuated to direct the remainder of the bone and/or cellular material into the other containers, at the discretion of the surgeon (e.g., again by using the transparent level with volume markings for each container).

At the completion of the reaming process, storage handle 41 may be easily removed from chamber 20 and labeled with any appropriate labels for further storage or processing of the material (e.g., at the biobank). Instrument 10 therefore provides a suitable means for collecting bone and/or cellular material during standard procedures in a sterile way, where such biologic materials are normally discarded.

In an optional embodiment, instrument 10 also includes a filter or mesh positioned in fluid communication with storage handle 41 so that the material extracted from the patient/donor can be filtered, as necessary. The filter or mesh allows instrument 10 to extract material that only meets certain defined criteria (e.g., particular sized bone chips, morsels, and/or marrow). In one example, each of the individual containers within storage handle 41 may include their own filters or meshes.

Figure 4:
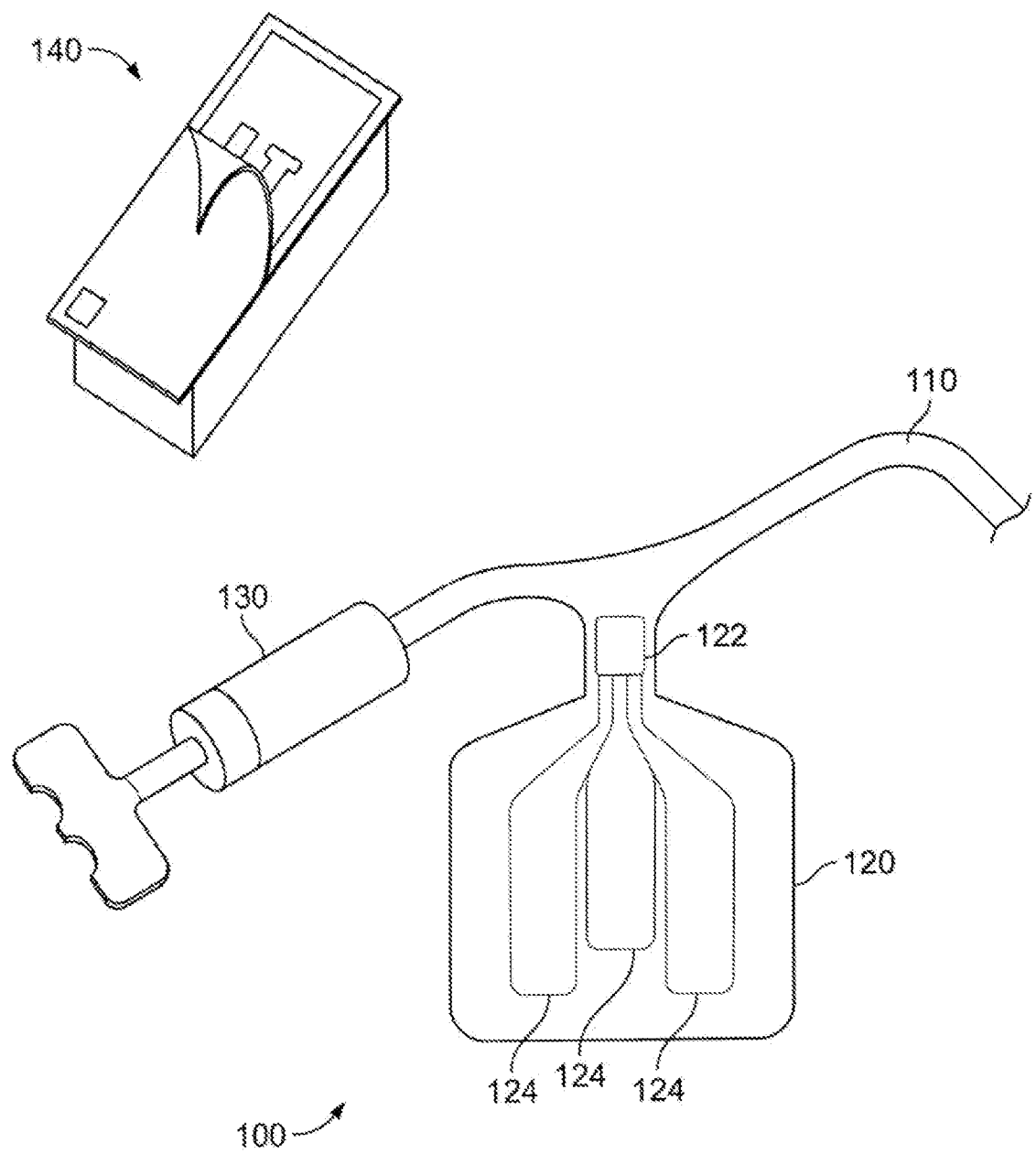
FIG. 4 is a plan view of a bone harvesting system according to another embodiment of the present invention.

An alternate embodiment of a bone harvesting system 100 is shown in FIG. 4. Harvesting system 100 includes a collection bag 120 for storing extracted bone and/or cellular material, and a manual suction device 130 (e.g., a syringe) for causing the bone and/or cellular material to move into collection bag 120. Alternatively, a powered suction device (not shown) could be used. A tube 110 is fluidly connected to collection bag 120 for moving bone and/or cellular material into bag 120. Tubing 110 leads into a multi-way valve 122 (e.g., a three-way valve), shown schematically in FIG. 4, which is effective to fluidly connect tube 110 to one of a number of pouches 124 within bag 120. Pouches 124 may be used to store bone and/or cellular material for different purposes (e.g., a pouch 124 for typification of the donor, a pouch 124 for testing the quality of the bone and/or cellular material, and a main storage pouch 124). As above, filters or meshes may be associated with each pouch 124 for filtering of the bone and/or cellular material.

In use, the surgeon may connect tube 110 to an instrument for reaming bone (not shown) or directly to the intramedullary canal of a patient's bone. During the reaming process, the surgeon may actuate suction device 130 to generate negative pressure in tube 110 and cause the bone and/or cellular material generated during the reaming process to move into tube 110 and subsequently to multi-way valve 122. At the surgeon's election, multi-way valve is then positioned in one of a number of locations, causing the extracted bone and/or cellular material to be deposited in one of pouches 124 within bag 120. In this manner, bone and/or cellular material may be extracted from a patient and positioned in bag 120 in a sterile manner. Indeed, as shown in FIG. 4, all of the components of bone harvesting system 100 may be placed in a single-use sterile package 140 for use by the surgeon in a sterile manner. Again, as above, it is to be understood that bone harvesting system 100 may be used in any of the methods disclosed in Applicant's '071 Application.

Figure 5:
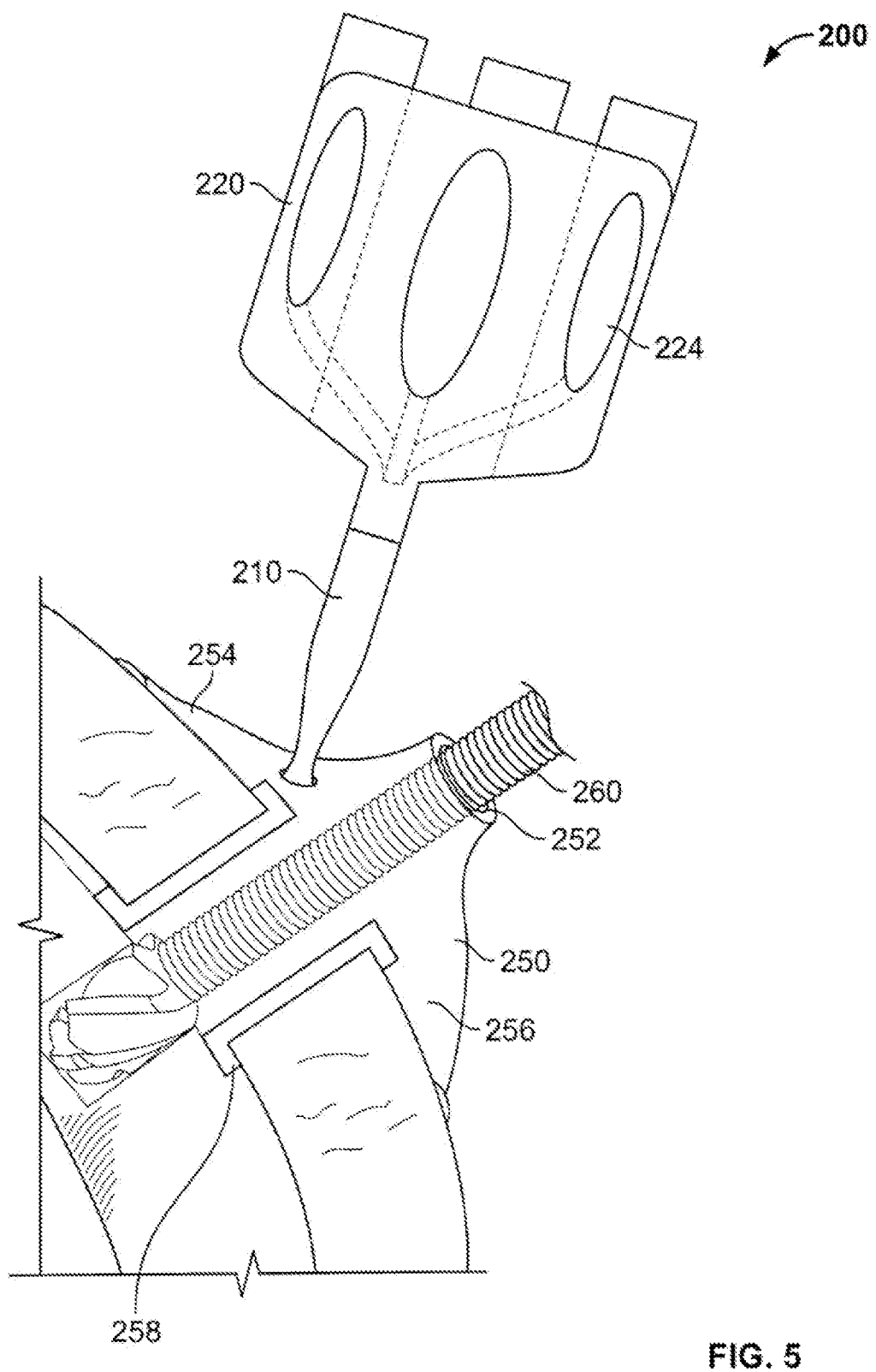
FIG. 5 is a partial cross-sectional view of a bone harvesting system according to yet another embodiment of the invention.

Yet another embodiment of a bone harvesting system 200 is shown in FIG. 5. As the embodiment shares commonalities with bone harvesting system 100, like numerals refer to like elements in this embodiment, but numbered in the 200s instead of the 100s.

Bone harvesting system 200 includes a collection bag 220 with a series of pouches 224 (e.g., three) therein, and a tube 210 fluidly connecting bag 220 to an instrument for reaming bone. As above, tube 210 may lead into a multi-way valve (e.g., a three-way valve, not shown) for diverting bone and/or cellular material into each of pouches 224. Filters or meshes may also be fluidly connected to each pouch 224 for filtering bone and/or cellular material.

Bone harvesting system 200 includes a sealing cover 250, optionally made of silicone, rubber, a polymer, or a polymer composite material suitable for creating a fluid-tight seal at the location of the patient's skin or tissue. Cover 250 has an opening 252 sized to receive a drill or reamer 260 therethrough, as shown in FIG. 5. As can be appreciated, opening 252, in an embodiment, is sized to be only slightly larger in diameter than the size of reamer 260 so as to allow a fluid-tight area to be maintained within sealing cover 250 during the reaming process. In a particular embodiment, reamer 260 may itself include a seal (not shown) that interacts with opening 252 and allows rotation of reamer relative to the seal to ensure a fluid-tight area is maintained within sealing cover 250 during reaming.

Sealing cover 250 also includes a set of legs 254, 256 extending from its body and arranged to contact the skin and/or tissue of a patient during the reaming process, as shown in FIG. 5. Legs 254, 256 are effective to establish and maintain a fluid-tight seal at the location of the patient's skin and/or tissue so that negative pressure generated within sealing cover 250 during the operation is maintained and reaming and extraction of bone and/or cellular material can proceed effectively. In an embodiment, legs 254, 256 may include a mild adhesive for adhering legs 254, 256 to the patient's skin and/or tissue during the operation to improve the quality of the seal.

In a further embodiment, sealing cover 250 also includes a tube or sleeve 258 extending from its body and into the incision site to establish a path for the bone and/or cellular material of the patient to travel. In an exemplary embodiment, sleeve 258 includes a flange at its end for engaging soft tissue and/or bone and securing sealing cover 250 relative thereto. Although not shown, a suction source is placed in fluid communication with bag 220 and/or sealing cover 250 to create negative pressure within sealing cover 250 and consequently draw bone and/or cellular material out of the patient and into bag 220.

In use, bone collection system 200 operates similar to the previous embodiments. A surgeon creates an initial incision in the patient and uses a guide wire to create a path to the bone to be reamed (e.g., a long bone). Reamer 260, which is cannulated in an embodiment, may then proceed over the guide wire and assist with directing sealing cover 250 attached thereto adjacent the patient's skin and/or tissue. The surgeon then docks sealing cover 250 against the patient's skin and/or tissue to create a fluid-tight seal at that location. Legs 254, 256 of sealing cover 250 are effective to assist in creating this seal. Further, in an embodiment, sleeve 258 extends through the patient's skin and tissue and adjacent the patient's bone. The surgeon may then ream the bone using reamer 260 and, as a consequence of the negative pressure created by the suction source (not shown), bone and/or cellular material generated during the reaming process may travel into sealing cover 250 and subsequently into pouches 224 of bag 220. The multi-way valve (not shown) may be used to direct bone and/or cellular material into each of the individual pouches 224, at the surgeon's discretion. Subsequently, if desired, pouches 224 may be closed off and individually separated from bag 220 (e.g., by pre-formed perforations) so that each pouch 224 may be used for its dedicated purpose (e.g., a pouch 224 for typification, a pouch 224 for quality control, and a pouch 224 for main storage). Of course, more or less pouches 224 may be included with bag 220 for other purposes.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It is also to be understood that individual features described in connection with certain embodiments can be shared with other embodiments, to the extent feasible. Further, the features of certain claims can also be shared with other claims, in any combination.

The invention claimed is:

1. A bone harvesting tool, comprising:
   a chamber housing defining first aperture, a second aperture spaced apart from the first aperture, an opening, a suction port arranged to be coupled to a suction source, and an internal cavity;
   a storage container fluidly connected to the opening of the chamber housing;
   a sleeve extending through the first aperture and establishing a fluid-tight seal with the chamber housing, the sleeve having a first diameter; and
   a reamer rotatable relative to the chamber housing including a shaft and a drilling tip, the shaft extending through the first aperture, the second aperture and the sleeve,
   wherein the shaft defines a second diameter smaller than the first diameter to allow bone and/or cellular material to pass in between the shaft and the sleeve and subsequently into the internal cavity of the chamber housing during reaming of a bone of the patient with the reamer.

2. The bone harvesting tool of claim 1, further comprising a first sealing member to establish the fluid-tight seal between the sleeve and the chamber housing.

3. The bone harvesting tool of claim 1, wherein the shaft of the reamer generally corresponds in size to the second aperture to establish a fluid-tight seal with the chamber housing.

4. The bone harvesting tool of claim 1, further comprising a second sealing member to assist in establishing the fluid-tight seal between the shaft of the reamer and the chamber housing.

5. The bone harvesting tool of claim 1, wherein the storage container is removably connectable to the opening of the chamber housing.

6. The bone harvesting tool of claim 5, wherein the storage container includes a first locking portion and the opening of the chamber housing includes a second locking portion, the first locking portion of the storage container being configured to lock with the second locking portion to secure the storage container to the chamber housing.

7. The bone harvesting tool of claim 1, further comprising a filter disposed within the storage container.

8. The bone harvesting tool of claim 1, further comprising the suction source fluidly connected to the chamber housing via the suction port to generate negative pressure within the internal cavity.

9. The bone harvesting tool of claim 1, wherein the drilling tip is fluted.

10. A bone harvesting tool, comprising:
   a chamber housing having a first aperture, a second aperture, an opening, an internal cavity and a port adapted to be fluidly connected to a fluid source;
   a sleeve extending through the first aperture;
   a reamer including a drilling tip and a shaft, the reamer being rotatable relative to the chamber housing, the shaft disposed at least partially within the sleeve and extending through the first and second apertures; and
   a storage container fluidly connected to the opening to receive bone and/or cellular material extracted during reaming of a bone of the patient with the reamer, the storage container including a first locking portion and the chamber housing including a second locking portion, the first locking portion being coupleable to the second locking portion to removably connect the storage container to the chamber housing.

11. The bone harvesting tool of claim 10, further comprising a suction source in fluid communication with the port configured to generate negative pressure within the internal cavity of the chamber housing.

12. The bone harvesting tool of claim 10, wherein the suction source is a powered suction source.

13. The bone harvesting tool of claim 10, further comprising a first sealing member disposed within the first aperture establishing a fluid-tight seal between the sleeve and the chamber housing.

14. The bone harvesting tool of claim 13, further comprising a second sealing member disposed within the second aperture establishing a fluid-tight seal between the shaft of the shaft of the reamer and the chamber housing.

15. The bone harvesting tool of claim 14, wherein at least one of the first and second sealing members comprises at least one of a rubber, silicone, polymer or polymer composite material.

16. The bone harvesting tool of claim 10, wherein the first and second apertures are diametrically positioned about the chamber housing such that the first and second apertures are defined by a common central axis.

17. The bone harvesting tool of claim 10, wherein the shaft of the reamer includes a proximal portion having a connector configured to couple to an instrument for rotating the reamer.

18. The bone harvesting tool of claim 17, wherein the connector is keyed for engaging the instrument for rotating the reamer.

19. The bone harvesting tool of claim 18, further comprising a guide wire.

20. The bone harvesting tool of claim 10, wherein the reamer is cannulated and configured to receive a guide wire.

\* \* \* \* \*